(12) United States Patent
Hayashi et al.

(10) Patent No.: US 7,829,500 B2
(45) Date of Patent: *Nov. 9, 2010

(54) PLANT-ACTIVATING AGENT

(75) Inventors: Masaharu Hayashi, Osaka (JP);
Tadayuki Suzuki, Wakayama (JP);
Toshio Hayashi, Wakayama (JP);
Masatoshi Kamei, Wakayama (JP);
Kazuhiko Kurita, Wakayama (JP)

(73) Assignee: Kao Corporation, Tokyo (JP)

( * ) Notice: Subject to any disclaimer, the term of this patent is extended or adjusted under 35 U.S.C. 154(b) by 1649 days.

This patent is subject to a terminal disclaimer.

(21) Appl. No.: 09/842,896

(22) Filed: Apr. 27, 2001

(65) Prior Publication Data

US 2002/0039971 A1 Apr. 4, 2002

(30) Foreign Application Priority Data

Apr. 28, 2000 (JP) ............................ 2000-131667
Apr. 28, 2000 (JP) ............................ 2000-131668
Apr. 28, 2000 (JP) ............................ 2000-131669

(51) Int. Cl.
*A01N 59/00* (2006.01)
*A01N 59/14* (2006.01)
*A01N 37/00* (2006.01)

(52) U.S. Cl. ...................... 504/119; 504/122; 504/125; 504/313

(58) Field of Classification Search ................. 504/313, 504/320, 119, 122, 125
See application file for complete search history.

(56) References Cited

U.S. PATENT DOCUMENTS

| | | | |
|---|---|---|---|
| 4,394,149 A * | 7/1983 | Szoka et al. .................... 71/28 |
| 4,626,277 A | 12/1986 | Suzuki et al. | |
| 4,681,900 A | 7/1987 | Iwasaki | |
| 5,482,529 A | 1/1996 | Ahlnas et al. | |
| 5,674,897 A * | 10/1997 | Kim et al. ..................... 514/552 |
| 6,489,269 B1 * | 12/2002 | Hayashi et al. .............. 504/353 |
| 6,849,576 B2 * | 2/2005 | Suzuki et al. ............. 504/116.1 |
| 6,884,759 B2 * | 4/2005 | Hayashi et al. .............. 504/353 |
| 2001/0019728 A1 * | 9/2001 | Basinger et al. .............. 424/667 |

FOREIGN PATENT DOCUMENTS

| | | | |
|---|---|---|---|
| BE | 892 401 | | 7/1982 |
| BE | 892401 | * | 7/1982 |
| DE | 32 34 610 A1 | | 3/1984 |
| DE | 37 24 595 A1 | | 2/1989 |
| DE | 44 45 546 A1 | | 6/1996 |
| DE | 4445546 | * | 6/1996 |
| EP | 0161114 | | 11/1985 |
| EP | 0167026 | | 1/1986 |
| EP | 0 539 980 A1 | | 5/1993 |
| EP | 0 544 518 A1 | | 6/1993 |
| FR | 2 501 005 | | 9/1982 |
| GB | 2116960 | * | 10/1983 |
| GB | 2228941 (ABS) | * | 12/1990 |
| JP | 50-129361 | | 10/1975 |
| JP | 50129361 | * | 10/1975 |
| JP | 55100304 | | 7/1980 |
| JP | 61021039 | | 1/1986 |
| JP | 62242604 | | 10/1987 |
| JP | 4031382 | | 2/1992 |
| JP | 08157819 (ABS) | * | 6/1996 |
| JP | 9512274 | | 12/1997 |
| WO | WO 83/03041 A1 | | 9/1983 |
| WO | WO 96/19111 A1 | | 6/1996 |
| WO | WO-00/02451 | * | 1/2000 |
| WO | WO 00/02451 A1 | | 1/2000 |
| WO | WO 01/58262 A1 | | 8/2001 |
| WO | WO 01/64832 A2 | | 9/2001 |

OTHER PUBLICATIONS

Welebir, Effective crop yield enhancing formulations containing fatty acids, fatty esters and calcium +2, Proceedings—Plant Growth Regulation Society of America, 1984, 11th, 270-5).*

Welebir, Effective crop yield enhancing formulations containing fatty acids, fatty esters and calcium +2, Instrum. Anal. Foods: Recent Prog., Proc. Symp. Int. Flavor Conf., 3rd, 1983, vol. 1, pp. 339-355.*

Reddy, P. S. et al., "Differential formation of octadecadienoic acid and octadecatrienoic acid products in control and injured/infected potato tubers," Biochimica et Biophysica Acta, vol. 1483, pp. 294-300, (2000).

XP-002215507 (Abstract), Ozeretskovskaya O.L., et al., "Mechanisms of elicitor-induced systemic resistance of plants to diseases," Fiziologiya Rastenii (Moscow), pp. 626-633, (1994).

XP-002215508 (Abstract), Watanabe, N. et al., "Activation of 20S proteasomes from spinach leaves by fatty acids," Plant and Cell Physiology, vol. 37, No. 2, pp. 147-151, (1996).

XP-002215509 (Abstract), Conconi, A. et al., "The octadecanoid signalling pathway in plants mediates a response to ultraviolet radiation," Nature (London), vol. 383, pp. 826-829, (1996).

* cited by examiner

*Primary Examiner*—Alton N Pryor
(74) *Attorney, Agent, or Firm*—Birch, Stewart, Kolasch & Birch, LLP

(57) ABSTRACT

The present invention provides a plant-activating agent for improving the activity of plants efficiently without a chemical injury onto the plant. The plant-activating agent is selected from the group consisting of (1) an organic acid derivative which is derived from the organic acid having two functional groups and wherein at least one of the above-mentioned functional groups is bonded to a group containing 1 to 30 carbon atoms; (2) a compound represented by the formula (II):

$$RCOO(AO)_nX^1 \qquad (II)$$

wherein R represents an alkyl or alkenyl group having 11 to 29 carbon atoms; $X^1$ represents a hydrogen atom, an alkyl or acyl group having 1 to 30 carbon atoms, an alkenyl group having 2 to 30 carbon atoms, or a counter ion; AO represents at least one group selected from oxyethylene, oxyprolylene and oxybutylene groups and may be random or block; and n represents an average number of moles added and is zero to 30; and (3) a glycerol derivative. If necessary, the agent is used together with a surfactant, a fertilizer component or a chelating agent.

9 Claims, No Drawings

PLANT-ACTIVATING AGENT

TECHNICAL FIELD OF THE INVENTION

The present invention relates to a plant-activating agent, a plant-activating composition or a method of activating a plant by applying said composition or agent in the state of a solution or a solid to roots, stems, phylloplanes or fruits of a plant, such as spraying onto phylloplanes or irrigating into soil. Now, hereinafter, the term of "plant" means products that can be recognized from the term itself, vegetables, fruits, fruit trees, crops, bulbs, flowers, grass, herbs, plants defined in taxonomy, and so on.

It is added by the inventors of the invention that the term "plant growth" includes increasing the amount of growth, increasing the weight of a plant on both sides of the aboveground and the underground. "Plant growth" also includes further increasing greenness of leaves in terms of SPAD, increasing the height of grasses, improving harvest or crop, increasing photosynthesis, accelerating growth of green cells, improving absorption of a fertilizer, increasing sugar content and ascorbic acid of leaves and fruit. In more detail, it extends to improving: gloss of leaves, rising-up of leaves, firmness of leaves, an increased thickness of leaves, firmness of stem, short joints of stem, thickness of stem, whiteness of root, the number of fine roots, vivacity or strength of grasses or trees, gloss of fruit, size of fruit, fruiting, color of fruit, etc.

BACKGROUND ART

Various nutrient elements are necessary for growth of plants. It is known that a lack of some of the elements causes hindrance in the growth of plants. For example, the big three fertilizer components function as follows. Nitrogen is a component element of proteins, and phosphorus is a formation element of nucleic acid or phospholipid and further plays an important part in energy metabolism and synthetic or decomposing reaction of a substance. Potassium has a physiological action of substance metabolism or substance migration. If these main components are lacking, the growth of plants generally becomes poor. Calcium is an important component constituting plants and cells, and further plays an important part in maintenance of the balance of the metabolic system. The lacking state of calcium causes physiological troubles. Besides, various nutrients as follows are necessary for plants: magnesium, iron, sulfur, boron, manganese, copper, zinc, molybdenum, chlorine, silicon, sodium and the like.

Nutritious components such as nitrogen, phosphorus and potassium are applied as basal fertilizer or additional fertilizer. Alternatively, they are applied by diluting liquid fertilizer and irrigating the diluted fertilizer into soil or by spraying the diluted fertilizer onto phylloplanes. These fertilizers are necessary and/or essential for the growth of plants. However, even if they are applied at larger concentrations than some values, the growth of plants and the yield of the plants cannot be further improved.

However, it is an important theme in agricultural production to promote the growth of agricultural plants and increase the yield per unit area to strive for an increase in income. Various plant growth regulators have been developed and used to help meet this need. The plant growth regulators, the typical examples of which include gibberellin and auxin, are used to regulate growth reactions or form-producing reactions such as germination, rooting, expansion, flowering and bearing. When these regulators are used, a period or a concentration thereof for applying these regulators and a method of treating these regulators are complicated. Thus, the uses thereof are restrictive.

In order to solve such problems, JP-A 55-100304 discloses that a plant growth regulator characterized by comprising an organic acid as an effective component is useful for graminoids, leaf vegetables and root vegetables. JP-A 62-242604 also discloses that a composition for regulating plant growth, which comprises lactic acid, is useful for promoting growth and/or production of fruits and suppressing growth of undesired plants.

Furthermore, U.S. Pat. No. 5,482,529 discloses a preparation for fertilizer comprising a plant nutrient, water, a lipophilic organic material and a fatty acid having 1 to 10 carbon atoms in order to improve absorbing phosphoric acid. JP-A 4-31382 also discloses that propionic acid or a polyhydric carboxylic acid makes a phosphoric acid-absorbing effect high.

JP-A 9-512274 discloses a method for regulating plant growth which comprises suppressing a height of the plant by applying a growth-suppressing composition comprising a polyol in an effective amount for growth-suppression to a root sphere of the plant and then increasing the diameter of its stem.

In the present situation, however, none of the above-mentioned techniques can be said to be sufficient in their effects for practical use.

DISCLOSURE OF THE INVENTION

An object of the present invention is to suffer no chemical injury to a plant, to promote a green-degree of its leaves, its leaf-area and its rooting power and to heighten an efficiency for absorbing a fertilizer, thereby activating the plant and improving a yield and quality thereof.

The present invention is a plant-activating agent selected from the group consisting of
(1) an organic acid derivative which is derived from the organic acid having two functional groups and wherein at least one of the above-mentioned functional groups is bonded to a group containing 1 to 30 carbon atoms;
(2) a compound represented by the formula (II):

$$RCOO(AO)_nX^1 \qquad (II)$$

wherein R represents an alkyl or alkenyl group having 11 to 29 carbon atoms; $X^1$ represents a hydrogen atom, an alkyl or acyl group having 1 to 30 carbon atoms, an alkenyl group having 2 to 30 carbon atoms, or a counter ion; AO represents at least one group selected from oxyethylene, oxyprolylene and oxybutylene groups and may be random or block; and n represents an average number of molecules added and is zero to 30; and
(3) a glycerol derivative.

The organic acid derivative (1) is preferably a compound represented by the following formula (I):

$$A\text{-}(B)_a\text{-}C \qquad (I)$$

wherein A and C are independent each other and each thereof is a group selected from —COOX, —COOR¹,

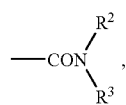

—R⁴, —OH, and —OR⁵; and

B is a group selected from —(CH₂)$_l$—, —(CH=CH)$_m$—,

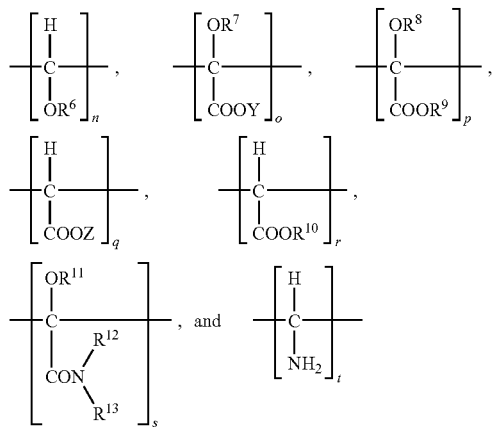

wherein each of X, Y and Z represents independently a hydrogen atom or a counter ion, each of R¹, R⁴ and R⁹ represents independently a hydrocarbon group having 1 to 30 carbon atoms, R⁵ is a group selected from

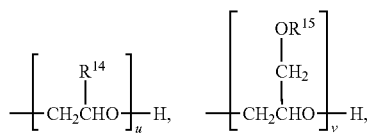

a hydrocarbon group having 1 to 30 carbon atoms and an acyl group having 1 to 30 carbon atoms, and each of R², R³, R⁶, R⁷, R⁸, R¹⁰, R¹¹, R¹², R¹³, R¹⁴ and R¹⁵ represents independently a hydrogen atom or a hydrocarbon group having 1 to 30 carbon atoms, a is zero or a number selected from 1 or more, each of l, m, n, o, p, q, r, s and t represents independently a number selected from zero to 10, each of u and v represents independently a number selected from 1 to 50; which are selected so that a group containing 1 to 30 carbon atoms may be bonded to at least one of the functional groups in the molecule; when both of A and C are groups selected from —R⁴, —OH and —OR⁵, B is not a group selected from —(CH₂)$_l$—, —(CH=CH)$_m$—,

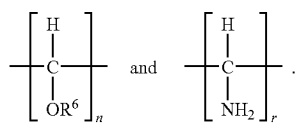

In the organic acid derivative (1), the organic acid preferably has at least one hydroxyl group as a functional group.

When the agent is the compound (2) represented by the formula (II), it is preferable in the formula (II) that n is zero to 20, R represents an alkyl or alkenyl group having 13 to 21 carbon atoms, X¹ represents a hydrogen atom, an alkyl or acyl group having 1 to 22 carbon atoms, an alkenyl group having 2 to 22 carbon atoms, or a counter ion (when n is not zero, the counter ion is not included).

When the agent is the glycerol derivative (3), the glycerol derivative is preferably selected from the group consisting of an ester of glycerol and an acid, an ether of glycerol and a hydroxyl group-containing compound, a condensate of glycerol or a derivative thereof, and glyceric acid or a derivative thereof.

Furthermore, the present invention provides a plant-activating composition comprising the above-mentioned plant-activating agent and at least one of a fertilizer agent, a surfactant and a chelating agent.

The above-mentioned surfactant is preferably selected from a nonionic surfactant, an anionic surfactant and an amphoteric surfactant.

The present invention also relates to a method of activating a plant by applying the above-mentioned plant-activating agent to the plant or use of the above-mentioned plant-activating agent for activating a plant.

Furthermore, the present invention relates to a method of promoting the green degree of leaves, a leaf-area and rooting power without a chemical injury by the above-mentioned plant-activating agent. It also relates a method of increasing the efficiency for absorbing a fertilizer by the above-mentioned plant-activating agent and further relates to a method of improving a yield and the quality of a plant by activating the plant.

Additionally, the present invention relates to a method of growing a plant by the above-mentioned plant-activating agent.

DETAILED DESCRIPTION OF THE INVENTION

Respective forms of the plant-activating agents (1), (2) and (3) of the present invention will be described. With regard to (1) the organic acid derivative having at least two functional groups wherein a group containing 1 to 30 carbon atoms is bonded to at least one of the functional groups.

In the present form, there is used an organic acid derivative having at least two functional groups wherein a group having 1 to 30 carbon atoms is bonded to at least one of the functional groups because of being able to give a plant activity efficiently without a chemical injury. The functional group includes carboxyl, hydroxyl and amino groups. The organic acid has preferably at least one hydroxyl group. The group bonded to the functional group includes an alkyl, alkenyl, alkylamino, oxyalkylene groups. The organic acid derivative is preferably a compound represented by the above-mentioned formula (I).

Each of R¹, R⁴ and R⁹ in the formula (I) represents a hydrocarbon group having 1 to 30 carbon atoms. R¹ and R¹² are preferably hydrocarbon groups having 12 to 26 carbon atoms and more preferably those having 14 to 22 carbon atoms. R⁴ is a hydrocarbon group having preferably 1 to 10 carbon atoms and more preferably 1 to 5 carbon atoms. R¹, R⁴ and R⁹ are preferably alkyl and alkenyl groups. The hydrocarbon group of R¹, R⁴ or R⁹, preferably alkyl or alkenyl group, may be saturated or unsaturated and are preferably saturated. It may be linear, branched or cyclic and is preferably linear or branched and more preferably linear. Specific examples of R¹, R⁴ and R⁹ include an alkyl group such as lauryl group, tetradecyl group, hexadecyl group, octadecy group, eicosyl group (which is an alkyl group having 20 carbon atoms) and behenyl group (which is an alkyl group having 22 carbon atoms); and an alkenyl group such as a C14F1 group (wherein the number next to C means the number of carbon atoms and the number next to F means the number of unsaturated bonds and this is the same hereinafter), a C16F1 group, a C18F1 group, a C20F1 group and a C22F1 group.

Each of $R^2$, $R^3$, $R^6$, $R^7$, $R^8$, $R^{10}$, $R^{11}$, $R^{12}$, $R^{13}$, $R^{14}$ and $R^{15}$ in the formula (I) represents a hydrogen atom or a hydrocarbon group having 1 to 30 carbon atoms, preferably 12 to 26 carbon atoms and more preferably 14 to 22 carbon atoms. It is preferably a hydrocarbon group. The hydrocarbon groups are preferably alkyl and alkenyl groups. The hydrocarbon group, preferably an alkyl or alkenyl group, may be saturated or unsaturated and preferably saturated. It may be linear, branched or cyclic, is preferably linear or branched, and is more preferably linear.

Each of X, Y and Z in the formula (I) represents a hydrogen atom or a counter ion. Specific examples of the counter ion include an alkali metal such as sodium and potassium, an alkali earth metal such as calcium and magnesium, an alkylamine salt such as trimethylamine and triethylamine, and an alkanolamine salt such as ethanolamine. An alkali metal or an alkali earth metal is preferable.

Moreover, a in the formula (I) is the total number of B. When at least two Bs are present in the formula (I), that is $a \geq 2$, B may be the same or different among the groups defined above.

The organic acid constituting the organic acid derivative in the present invention is preferably a hydroxycarboxylic acid such as citric acid, gluconic acid, malic acid, lactic acid or tartaric acid, and is more preferably citric acid.

When the organic acid derivative in the present invention has a hydrophilic group and a lipophilic group, its HLB measured by Griffin's method is preferably not more than 10, more preferably not more than 8, and most preferably not more than 5.

With regard to (2) the compound represented by the above-mentioned formula $RCOO(AO)_n X^1$ (II).

In the present form, R in the formula (II) has 11 to 29 carbon atoms, preferably 13 to 21 carbon atoms, and more preferably 15 to 19 carbon atoms because of being able to give a plant activity efficiently without a chemical injury. It may be saturated or unsaturated and is preferably saturated. On the other hand, it may be linear, branched or cyclic and is preferably linear or branched and more preferably linear. Specific examples of R include alkyl groups such as undecyl, tridecyl, pentadecyl, heptadecyl, nonadecyl and henicosyl groups, and alkenyl groups such as pentadecenyl, heptadecenyl and nonadecenyl groups. There are preferably alkyl groups such as pentadecyl, heptadecyl and nonadecyl groups, and alkenyl groups such as pentadecenyl, heptadecenyl and nonadecenyl groups. There are particularly preferably alkyl groups such as pentadecyl, heptadecyl and nonadecyl groups.

$X^1$ in the formula (II) represents a hydrogen atom, an alkyl or acyl group having 1 to 30 carbon atoms (preferably an alkyl or acyl group having 1 to 22 carbon atoms), an alkenyl group having 2 to 30 carbon atoms (preferably an alkenyl group having 2 to 22 carbon atoms), or a counter ion. Specific examples of $X^1$ include alkyl groups such as lauryl, tetradecyl, hexadecyl, octadecyl, arachinyl and behenyl groups; acyl groups such as lauroyl, myristoyl, palmitoyl, stearoyl, arachidoyl and behenoyl groups; and alkenyl groups such as tetradecenyl, hexadecenyl, oleyl, codoyl, eicosenyl and docosenyl groups. There are preferably alkyl groups such as hexadecyl, octadecyl and arachinyl groups; acyl groups such as palmitoyl, stearoyl and arachidoyl groups; and alkenyl groups such as hexadecenyl, oleyl, codoyl and eicosenyl groups. There are particularly preferably alkyl groups such as hexadecyl, octadecyl and arachinyl groups. Specific example of the counter ion may be one of alkali metals such as sodium and potassium; alkali earth metals such as calcium and magnesium; alkylamine salts such as trimethylamine and triethylamine; and alkanolamine salts such as ethanolamine. There are preferably alkali metals and alkali earth metals.

AO represents at least one group selected from oxyethylene, oxypropylene and oxybutylene groups. The number of AO units being n, AO's may be the same or different. It may be random or block, and n represents an average number of moles added of zero to 30, preferably zero to 20 and more preferably zero to 10. When the compound (II) has a hydrophilic group and a lipophilic group, its HLB measured by Griffin's method is preferably not more than 10, more preferably not more than 8, and most preferably not more than 5.

From the viewpoint of promoting the plant-growth, there is preferably one represented by the formula (II) wherein n is zero to 20, R is an alkyl or alkenyl group having 13 to 21 carbon atoms, X is a hydrogen atom, an alkyl or acyl group having 1 to 22 carbon atoms, an alkenyl group having 2 to 22 carbon atoms, or a counter ion (when n is not zero, the counter ion is excluded).

With regard to (3) the glycerol derivative.

In the present form, a glycerol derivative is used because of giving a plant activity efficiently without a chemical injury. The glycerol derivative is preferably selected from the group consisting of an ester of glycerol and an acid (referred to hereinafter as a glycerol ester), an ether of glycerol and a hydroxyl group-containing compound (referred to hereinafter as a glycerol ether), a condensate of glycerol or a derivative thereof, and glyceric acid or a derivative thereof.

The acid constituting the glycerol derivative may be an organic acid or an inorganic acid. The organic acid may have 1 to 30 carbon atoms, preferably 4 to 30 carbon atoms and more preferably 12 to 24 carbon atoms. The inorganic acid may be phosphoric acid, sulfuric acid or carbonic acid. When the ester of the inorganic acid is used, the inorganic acid may be in a salt form. The glycerol ester is preferably an ester of glycerol and an organic acid, that is, a monoester, diester or triester of glycerol and an organic acid. It is possible to use, as the triester of glycerol and an organic acid, a synthesized triester, an animal fat and/or oil such as beef tallow, pork lard, fish oil and whale oil, or a vegetable fat and/or oil such as coconut oil, palm oil, palm-stearin oil, castor oil, bean oil or olive oil. A fat and/or oil is preferable.

The hydroxyl group-containing compound constituting the glycerol ether may be an alcohol having 1 to 30 carbon atoms, preferably 4 to 30 and more preferably 12 to 24. The glycerol ester may be a glycerol monoalkyl ether such as batyl alcohol, isostearyl glyceryl ether and behenyl glyceryl ether. It may be diether or triether. The glycerol ether in the present invention includes an alkylene oxide (referred to hereinafter as AO) adduct to glycerol. The average number of AO moles added in the adduct is preferably 1 to 30, more preferably 1 to 10 and most preferably 1 to 5. An AO adduct to a mixture of glycerol and an oil and/or fat can be used. The average number of AO moles added in the adduct is preferably 1 to 30, more preferably 1 to 10 and most preferably 1 to 5.

The condensate of glycerol or a derivative thereof may be a polyglycerol represented by the following formula or a derivative thereof:

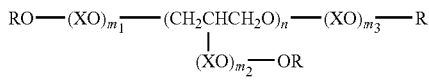

wherein n is a number selected from 2 to 50, R represents a hydrogen atom or an acyl group having 2 to 31 carbon atoms, X represents an alkylene group having 2 to 4 carbon atoms, and each of $m_1$, $m_2$ and $m_3$ is a number selected from zero to 30.

Glyceric acid can be obtained by oxidizing glycerol or glyceraldehyde. In the present invention, a glyceric acid derivative such as a glyceric acid ester and a glyceric acid amide may be also used.

When the glycerol derivative in the present invention has a hydrophilic group and a lipophilic group, its HLB measured by Griffin's method is preferably not more than 10, more preferably not more than 8, and most preferably not more than 5.

The form of the above-mentioned plant-activating agent may be any one of liquid, flowable, wettable powder, granule, dust formulation and tablet. When the agent is treated as an aqueous solution or an aqueous dispersion, the plant-activating agent is usually diluted into a concentration of 0.01 to 5000 ppm, preferably 0.1 to 1000 ppm, and more preferably 0.5 to 500 ppm to be applied onto phylloplanes or roots of a plant.

For the method supplying the plant-activating agent of the present invention to a plant, various techniques may be used. For example, it includes a method of applying directly a dust formulation or a granule as a fertilizer, a method of spraying a diluted aqueous solution directly on phylloplanes, stems or fruits of a plant, a method of injecting a diluted aqueous solution into soil, and a method of supplying to dilute and to mix into a liquid for hydroponics and a supplying water which are contacted with roots and which are such as hydroponics and a rock wool.

Plants, which can be treated with the plant-activating agent of the present invention, may be fruit vegetables such as a cucumber, a pumpkin, a watermelon-plant, a melon, a tomato, an eggplant, a green pepper, a strawberry, an okra, kidney beans in a pod, a broad bean, a pea, green soybeans in a pod and a corn; leaf vegetables such as a Chinese cabbage, greens for pickling, a *Brassica campestris* (a Chinese spinach-like green vegetable), a cabbage, a cauliflower, a broccoli, a Brussels sprout, an onion, a Welsh onion, a garlic, a scallion, a leek, an asparagus, a lettuce, a green for salad (which is called Saladana in Japan), a celery, a spinach, a crown daisy, a parsley, a trefoil (which is called Mitsuba in Japan and is useful as herb), a dropwort, an udo (which is an *Aralia cordata*), a Japanese ginger, a Japanese butterbur and a labiate; and root vegetables such as a radish, a turnip, a burdock, a carrot, a potato, a taro, a sweet potato, a yam, a ginger-plant (which is called Shoga in Japan) and a lotus root. Besides, the plant-activating agent may be used for a rice-plant, a barley, a wheat or a group thereof, and petalous-plants.

For the purpose of promoting emulsification, dispersion, solubilization or permeation, it is preferable in the present invention to use the following surfactant together with the plant-activating agent. There are exemplified nonionic surfactants, anionic surfactants, cationic surfactants and amphoteric surfactants. Nonionic surfactants, anionic surfactants and amphoteric surfactants are preferable.

The nonionic surfactants are sorbitan fatty acid esters, polyoxyalkylene sorbitan fatty acid esters, polyoxyalkylene fatty acid esters, glycerol fatty acid esters, polyoxyalkylene glycerol fatty acid esters, polyglycerol fatty acid esters, polyoxyalkylene polyglycerol fatty acid esters, sucrose fatty acid esters, resin acid esters, polyoxyalkylene resin acid esters, polyoxyalkylene alkyl ethers, polyoxyalkylene alkylphenyl ethers, alkyl(poly)glycosides and polyoxyalkylenealkyl (poly)glycosides. There are preferably exemplified an ether group-containing nonionic surfactant having no nitrogen atom and an ester group-containing nonionic surfactant.

The anionic surfactants are carboxylic, sulfonic, sulfuric ester group-containing and phosphoric ester group-containing surfactants.

Examples of the carboxylic surfactants include fatty acids having 6 to 30 carbon atoms or salts thereof, polyhydric carboxylic acid salts, polyoxyalkylene alkyl ether carboxylic acid salts, polyoxyalkylene alkylamide ether carboxylic acid salts, rhodinic acid salts, dimmer acid salts, polymer acid salts and tall oil fatty acid salts.

Examples of the sulfonic surfactants include alkylbenezenesulfonates, alkyl sulfonates, alkylnaphthalenesulfonates, naphthalenesulfonates, diphenyl ether sulfonic acid salts, condensates of alkylnaphthalenesulfonates and condensates of naphthalenesulfonates.

Examples of the sulfuric ester group-containing surfactants include alkylsulfates, polyoxyalkylene alkylsulfates, polyoxyalkylene alkyl phenyl ether sulfuric acid salts, tristyrenated phenol sulfuric acid ester salts, polyoxyalkylene distyrenated phenol sulfuric acid ester salts and alkylpolyglycoside sulfuric acid salts.

Examples of phosphoric acid ester group-containing surfactants include alkyl phosphoric acid ester salts, alkylphenylphosphoric acid ester salts, polyoxyalkylene alkylphosphoric acid ester salts and polyoxyalkylene alkylphenylphosphoric acid ester salts.

Examples of the salts include salts of metals (such as Na, K, Ca, Mg and Zn), ammonium salts, alkanolamine salts and aliphatic amine salts.

The amphoteric surfactants are amino acid group-containing, betaine group-containing, imidazoline group-containing and amine oxide group-containing surfactants.

Examples of the amino acid group-containing surfactants include acylamino acid salts, acylsarcosine acid salts, acyloylmethylaminopropionic acid salts, alkylaminopropionic acid salts and acylamide ethylhydroxyethylmethylcarboxylic acid salts.

Examples of the betaine group-containing surfactants include alkyldimethylbetaine, alkylhydroxyethylbetaine, acylamide propylhydroxypropylammonia sulfobetaine and ricinoleic acid amide propyl dimethylcarboxymethylammonia betaine.

Examples of the imidazoline group-containing surfactants include alkylcarboxymethylhydroxyethyl imidazolinium betaine and alkylethoxycarboxymethyl imidazolinium betaine.

Examples of the amine oxide group-containing surfactants include alkyldimethylamine oxide, alkyldiethanolamine oxide and alkylamidepropylamine oxide.

One kind of the above-mentioned surfactants may be used, and a mixture of two or more kinds thereof may be used. When one of these surfactants comprises a polyoxyalkylene group, it is exemplified that the polyoxyalkylene group has a polyoxyethylene group and the average number of moles added of alkylene oxide is from 1 to 50. To solubilize and disperse uniformly effective components of the plant-activating agent, the surfactant is preferably a highly hydrophilic surfactant and its HLB measured by Griffin's method is preferably not less than 10 and more preferably not less than 12.

The following fertilizer components may be used together therewith. There are specifically exemplified inorganic or organic compounds which can supply elements such as N, P, K, Ca, Mg, S, B, Fe, Mn, Cu, Zn, Mo, Cl, Si and Na, in particular N, P, K, Ca and Mg. The inorganic compounds are ammonium nitrate, potassium nitrate, ammonium sulfate, ammonium chloride, ammonium phosphate, sodium nitrate, urea, ammonium carbonate, potassium phosphate, calcium superphosphate, fused phosphate fertilizer ($3MgO \cdot CaO \cdot P_2O_5 \cdot 3CaSiO_2$), potassium sulfate, potassium chloride, nitrate of lime, slaked lime, carbonate of lime, magnesium sulfate, magnesium hydroxide and magnesium carbonate. The organic compounds are fowl droppings, cow dung, Bark compost, amino acid, peptone, amino acid solution (which is called Mieki in Japan), fermentation extracts, calcium salts of organic acids (such as citric acid, gluconic acid and succinic acid), and calcium salts of fatty acids (such as formic acid, acetic acid, propionic acid, caprylic acid, capric acid and caproic acid). These fertilizer components may be used together with the surfactant. When fertilizer components are sufficiently applied as basal fertilizer to soil as seen in outdoor cultivation of a rice-plant or vegetables, it is unnecessary to mix the fertilizer components. Further, when a cultivation form is such as a fertigation (a hydroponic soil culture) or hydroponics, when it avoids applying excessively basal fertilizer and, when it is a type of providing a fertilizer component together with irrigation-water, the fertilizer component is preferably mixed.

When the plant-activating composition of the present invention is mixed with a chelating agent which are the following organic acid having chelating ability and a salt thereof, the growth and the efficiency for absorbing a fertilizer are further improved. The chelating agents are oxycarboxylic acids such as citric acid, gluconic acid, malic acid, heptonic acid, oxalic acid, malonic acid, lactic acid, tartaric acid, succinic acid, fumaric acid, maleic acid, adipic acid and glutaric acid; polycarboxylic acids; and salts thereof such as potassium salt, sodium salt, alkanolamine salt and aliphatic amine salt.

Mixing a chelating agent other than the organic acids also causes the growth and the efficiency for absorbing a fertilizer to be improved. The chelating agent to be mixed are aminocarboxylic group-containing chelating agents such as ethylenediaminetetraacetic acid (EDTA), nitrilotriacetic acid (NTA) and cyclohexanediaminetetraacetic acid (CDTA).

In the present invention, at least one selected from a fertilizer component, a surfactant and a chelating agent may be used together therewith. It is particularly preferable to use both of a surfactant and a chelating agent together therewith. If a fertilizer is required at the time of application thereof, it is preferable to use a surfactant, a fertilizer and a chelating agent together with the plant-activating agent of the present invention, for example. If no fertilizer is required at the time of application thereof, it is preferable to use a surfactant and a chelating agent together the plant-activating agent of the present invention, for example.

The form of and the method spraying the plant-activating agent of the present invention and so on are the same as in the above-mentioned description. As necessary, water and/or a solvent may be comprised.

About the ratio of the respective components in the plant-activating composition of the present invention, 10 to 20000 parts by weight and particularly 100 to 2000 parts by weight of a surfactant, zero to 50000 parts by weight and particularly 10 to 5000 parts by weight of a fertilizer component, zero to 10000 parts by weight and particularly 10 to 5000 parts by weight of a chelating agent, and zero to 50000 parts by weight and particularly 10 to 5000 parts by weight of other nutrients (such as sacchrides, amino acids, vitamins) are preferable per 100 parts by weight of the activating agent.

When the activating agent in a dust formulation or granule state as a fertilizer is generally applied to soil, it is preferable to use the dust formulation or granule containing the above-mentioned components other than water at the same ratio as above. This dust formulation or granule may contain a vehicle to prevent caking thereof.

Treated by the plant-activating agent of the present invention in an appropriate concentration, the activity of a plant can be efficiently improved without a chemical injury to the plant. Thus, the plant-activating agent can be used for various farm products. Furthermore, the present invention causes improvement in plant-growth, such as promotion of taking root of a plant, increase of SPAD value, and increase of the efficiency for absorbing a fertilizer. Germination of seeds of a plant is promoted.

EXAMPLES

Examples of the present invention will be described hereinafter. Examples 1 to 4, Examples A1 to A4, and Examples B1 to B4 represent examples with regard to (1), (2) and (3), respectively.

Example 1

<Test of Reproductive Ability Using Chlorella Cells>

Chlorella cells which were green cells of a higher plant were cultured with vibration in an inorganic salt medium. The reproductive ability using chlorella cells (ability for increasing the number of the cells) was evaluated by comparing the treated area to which the plant-activating agent or the plant-activating composition shown in Table 1 was added in an effective concentration shown in Table 1 with non-treated area (i.e., only original nutrients of the inorganic salt medium). The concentration of the cells was set to $1.00 \times 10^5$ (cells per ml) at the start of the test. The reproductive ability of the cells is respected by each of the relative values in the number of the chlorella cells after 14 days from adding the respective plant-activating agents or compositions followed by culturing the cells when the number of cells on the non-treated area is made to be 100. As the inorganic salt medium, a Linsmaier-Skoog (LS) medium was used. Three media were used as the treated areas and the non-treated areas every the plant-activating agent or the plant-activating composition. The average thereof was compared with that in the non-treated areas.

TABLE 1

| | | Plant-activating agent or plant-activating composition | | Evaluation result |
|---|---|---|---|---|
| | | Kind | Concentration (ppm) | Reproductive ability |
| Inventive product | 1-1 | Citric acid C18 monoester | 30 | 142 |
| | 1-2 | Citric acid C18 monoester | 15 | |
| | | Citric acid C16 monoester | 15 | 140 |
| | 1-3 | Citric acid C18 monoester potassium salt | 30 | 138 |
| | 1-4 | Citric acid C18 monoester | 30 | |
| | | EDTA . 4Na | 4 | 148 |

TABLE 1-continued

| | | Plant-activating agent or plant-activating composition | | Evaluation result |
|---|---|---|---|---|
| | | Kind | Concentration (ppm) | Reproductive ability |
| | 1-5 | Citric acid C18 monoamide | 30 | 139 |
| | 1-6 | Citric acid C14 monoamide | 30 | 136 |
| | 1-7 | Citric acid C18 diester | 30 | 138 |
| | 1-8 | Citric acid C12 monoamide | 30 | 128 |
| Comparative product | 1-1 | Lactic acid | 30 | 99 |
| | 1-2 | Inorganic salt medium (non-treated area) | — | 100 |

(Note) C18 or the like means an alkyl group in which the number of carbon atoms is the number next to C. (This is the same hereinafter.)

Example 2

<Test of Hydroponics of Tomato Seedlings>

Seeds of tomato "Momotaro" were sown in a box, and seedlings having 3 true leaves at the expansion period were hydroponically used in a culturing solution in which "OKF2" (supplied by Otsuka Chemical Co., Ltd.) as a fertilizer (an NPK base) was diluted [to 538 times (i.e. 855 ppm as an effective fertilizer component)]. At this time, plant-activating compositions comprising components shown in Table 2 in effective component concentrations shown in Table 2 were added to carry out the test. Each of the used plant-activating compositions was forcibly emulsified with a home mixer to be used. After 6 days from starting the test, the culturing solution was collected to measure the concentration of nitrate ions with RQ Flex (supplied by Merk) and to calculate the efficiency for absorbing a nitrate nitrogen fertilizer. At this time, plural containers in which hydroponics was carried out as described above were prepared and then the concentration of nitrate ions was measured one time about each of three containers that were arbitrarily selected. Three data were obtained about the respective areas and then the average of the calculated efficiencies of the absorption was defined as the efficiency for absorbing the nitrate nitrogen fertilizer. About the three individuals used in the measurement of the efficiency for absorbing the fertilizer, their chlorophyll values (hereinafter abbreviated to SPAD values) showing the green degree of leaves were measured with SPAD502 supplied by Minolta Co., Ltd. SPAD value was measured 10 times for each of the three individuals (that is, the number of data is 30). The average thereof was made as SPAD value. The SPAD value was measured at different positions of the third true leaf in each of the individuals.

These results are shown in Table 2. Each and all thereof are the relative values when that of the non-treated areas are made to be 100.

The fertilizer composition of "OKF2" (Otsuka Chemical Co., Ltd.) was as follows: N:P:K:Ca:Mg=14:8:16:6:2.

TABLE 2

| | | Plant-activating composition | | Test result | |
|---|---|---|---|---|---|
| | | Kind | Concentration (ppm) | Efficiency for absorbing a fertilizer | SPAD value |
| Inventive product | 2-1 | Citric acid C16 diester | 100 | 137 | 113 |
| | | POE(20) sorbitan monooleate | 500 | | |
| | 2-2 | Citric acid C18 monoester | 50 | 140 | 118 |
| | | POE(20) sorbitan monooleate | 150 | | |
| | 2-3 | Citric acid C18 monoester | 50 | 142 | 120 |
| | | POE(20) sorbitan monooleate | 150 | | |
| | | EDTA.4Na | 20 | | |
| | 2-4 | Citric acid C18 monoamide | 100 | 134 | 109 |
| | | POE(20) sorbitan monooleate | 300 | | |
| | 2-5 | Citric acid C18 diester | 400 | 139 | 124 |
| | | POE(20) sorbitan monooleate | 400 | | |
| | 2-6 | Citric acid C18 monoamide | 100 | 138 | 117 |
| | | POE(20) sorbitan monooleate | 200 | | |
| | | Malonic acid | 30 | | |
| | 2-7 | Citric acid C14 monoester | 100 | 134 | 112 |
| | | POE(20) sorbitan monooleate | 150 | | |
| | 2-8 | Citric acid C20 monoester potassium salt | 100 | 138 | 119 |
| | | POE(20) sorbitan monooleate | 200 | | |
| | 2-9 | Citric acid C18F1 monoester | 100 | 136 | 116 |
| | | POE(20) sorbitan monooleate | 200 | | |
| | 2-10 | Citric acid C18 monoester sodium salt | 40 | 134 | 115 |
| | | POE(20) sorbitan monooleate | 250 | | |
| | 2-11 | Citric acid C16 monoester potassium salt | 100 | 132 | 113 |
| | | POE(20) sorbitan monooleate | 250 | | |
| Comparitive product | 2-1 | Lactic acid | 100 | 98 | 100 |
| | | POE(20) sorbitan monooleate | 200 | | |
| | 2-2 | Culturing solution only (non-treated area) | — | 100 | 100 |

(Notes) In the Table, POE is an abbreviation of polyoxyethylene. The number in the parentheses is the average number of ethylene oxide moles added. (This is the same hereinafter.)

Example 3

<Test of Soil-Treatment for Tomatoes>

Seeds of tomato "Momotaro" were sown in a cell tray using "Kureha Engei Baido" [horticultural soil supplied by Kureha Chemical Industry Co., Ltd.; the fertilizer components: N:P:K=0.4:1.9:0.6 (g/kg)] as the cultural soil. After cotyledons of the plants expanded, the plants were fixedly planted in pots having a diameter of 15 cm. Then, the plant-activating compositions comprising components shown in Table 3 and 460 ppm (1000-fold diluted solution) of "OKF2" (supplied by Otsuka Chemical Co., Ltd.) (wherein the balance is water) were given in a treating amount of 100 ml per individual at intervals of 7 days. At this time, each of the plant-activating compositions used were forcibly emulsified with a home mixer. This treatment was repeated 5 times. After 6 days from finishing the 5 treatments, the fresh-weight of the plants was measured. Then, the SPAD value thereof was measured by the same manner as in Example 2. In the present example, however, the number of the used individual was 10, the result of the fresh-weight was the average of 10 data thereof, and the result of the SPAD value was the average of 30 data thereof (that is, 3 points every individual were measured). The SPAD value was measured about the third true leaf. These results are shown in Table 3 provided that each and all are represented by the relative value when that of the non-treated medium is made to be 100.

Example 4

<Test of Soil-Treatment for Spinach>

Seeds of spinach "Esper" were sown in a cell tray having 50 holes with using "Takii soil for seeds" [Takii & Company LTD, fertilizer components: N:P:K=480:760:345 (mg/l), pH 6.4, and EC: 0.96] as a culturing soil. One area for the test has 10 holes (n=10) in the cell tray. After cotyledons of the plants expanded, the treatment started. That is, the plant-activating composition comprising components shown in Table 4 at effective component concentrations shown in Table 4 (wherein the balance is water) were given in a treating amount of 10 ml per 100 individuals at intervals of 7 days (in case of treated areas). At this time, each of the plant-activating compositions used was forcibly emulsified with a home mixer. This treatment was repeated 4 times. After 6 days from finishing the 4 treatments, the fresh-weights and SPAD values of the plants were measured in the same manner as in Example 2. In the present example, however, the number of the used individuals was 10, the result of the fresh-weight was the average of 10 data thereof, and the result of the SPAD value was the average of 30 data thereof (that is, 3 points every individual were measured). The SPAD value was measured about the second true leaf. These results are shown in Table 4 provided that each and all are represented by the relative value when that of the non-treated area is made to be 100.

During the test period, additional fertilization of fertilizer components was not carried out. Therefore, the plants absorbed and utilized only the nutrients comprised in the culturing soil.

TABLE 3

| | | Plant-activating composition | Concentration (ppm) | Test result | |
|---|---|---|---|---|---|
| | | Kind | | Fresh-weight | SPAD value |
| Inventive product | 3-1 | Citric acid C18 monoamide | 50 | 116 | 113 |
| | | POE(20) lauryl ether | 150 | | |
| | 3-2 | Citric acid C18 monoester | 50 | 124 | 127 |
| | | POE(8) oleyl ether | 150 | | |
| | 3-3 | Citric acid C16 monoester | 50 | 120 | 122 |
| | | POE(20) sorbitan monooleate | 150 | | |
| | 3-4 | Citric acid C16 monoester | 50 | 122 | 124 |
| | | POE(20) sorbitan monooleate | 150 | | |
| | | EDTA.4Na | 20 | | |
| | 3-5 | Citric acid C18 monoester potassium salt | 50 | 119 | 120 |
| | | POE(6) sorbitan monolaurate | 150 | | |
| | 3-6 | Citric acid C20 monoester | 50 | 122 | 123 |
| | | POE(40) sorbit tetraoleate | 150 | | |
| | 3-7 | Citric acid C20 monoester potassium salt | 50 | 117 | 114 |
| | | Alkyl glycoside (MYDOL 12 supplied by Kao Corp.) | 150 | | |
| | 3-8 | Citric acid C20 monoester potassium salt | 50 | 120 | 116 |
| | | Alkyl glycoside (MYDOL 12 supplied by Kao Corp.) | 150 | | |
| | | Succinic acid | 20 | | |
| | 3-9 | Citric acid C16 monoamide | 50 | 114 | 112 |
| | | Sodium POE(3) lauryl ether sulfate | 150 | | |
| | 3-10 | Citric acid C18F1 monoester | 50 | 120 | 120 |
| | | Sodium POE(4.5) lauryl ether acetate | 150 | | |
| | 3-11 | Citric acid C18 diester | 50 | 121 | 121 |
| | | Lauryl amide propyl betaine | 150 | | |
| Comparative product | 3-1 | Lactic acid | 50 | 99 | 100 |
| | | Sodium POE(3) lauryl ether sulfate | 150 | | |
| | 3-2 | Treated with liquid fertilizer (non-treated area) | — | 100 | 100 |

TABLE 4

| | | Plant-activating composition | | Test result | |
|---|---|---|---|---|---|
| | | kind | Concentration (ppm) | Fresh-weight | SPAD value |
| Inventive product | 4-1 | Citric acid C18 diester<br>POE(20) lauryl ether | 100<br>200 | 135 | 123 |
| | 4-2 | Citric acid C18 monoester potassium salt<br>POE(8) oleyl ether | 100<br>200 | 135 | 126 |
| | 4-3 | Citric acid C18 monoamide<br>POE(20) sorbitan monooleate | 100<br>200 | 134 | 132 |
| | 4-4 | Citric acid C18 monoamide<br>POE(20) sorbitan monooleate<br>EDTA.4Na | 100<br>200<br>30 | 138 | 130 |
| | 4-5 | Citric acid C18 monoester<br>POE(6) sorbitan monolaurate | 100<br>200 | 136 | 128 |
| | 4-6 | Citric acid C20 monoester<br>POE(40) sorbit tetraoleate | 100<br>200 | 130 | 123 |
| | 4-7 | Citric acid C16 monoester<br>Alkyl glycoside (MYDOL 12 supplied by Kao Corp.) | 100<br>200 | 128 | 124 |
| | 4-8 | Citric acid C16 monoester<br>Alkyl glycoside (MYDOL 12 supplied by Kao Corp.)<br>Malic acid | 100<br>200<br>30 | 134 | 126 |
| | 4-9 | Citric acid C12 monoamide<br>Sodium POE(3) lauryl ether sulfate | 100<br>200 | 127 | 117 |
| Comparative product | 4-1 | Lactic acid<br>Sodium POE(3) lauryl ether sulfate | 100<br>200 | 98 | 100 |
| | 4-2 | Treated by water (non-treated area) | — | 100 | 100 |

Example A1

<Test of Reproductive Ability Using Chlorella Cells>

Example A2

<Test of Hydroponics of Tomato Seedlings>

Example A3

<Test of Soil-Treatment for Tomatoes>

Example A4

<Test of Soil-Treatment for Spinach>

Examples A1 to A4 were carried out by the same manner as in Examples 1 to 4 except that the plant-activating agents described in Tables A1 to A4 were used. Results are shown in Tables A1 to A4 respectively.

TABLE A1

| | | Plant-activating agent or plant-activating composition | | Evaluation result |
|---|---|---|---|---|
| | | Kind | Concentration (ppm) | reproductive ability |
| Inventive product | A1-1 | Myristic acid (LUNAC MY-98) | 30 | 127 |
| | A1-2 | Myristic acid (LUNAC MY-98)<br>Palmitic acid (LUNAC P-95) | 15<br>15 | 146 |
| | A1-3 | Stearic acid (LUNAC S-98) | 30 | 154 |
| | A1-4 | Stearic acid (LUNAC S-98)<br>EDTA.4Na | 30<br>4 | 158 |
| | A1-5 | Oleic acid | 30 | 148 |
| | A1-6 | Behenic acid (LUNAC BA) | 30 | 150 |
| | A1-7 | Melissic acid | 30 | 138 |
| Comparative product | A1-1 | Acetic acid | 30 | 90 |
| | A1-2 | Acetic acid<br>Ascorbic acid Na salt | 30<br>4 | 92 |
| | A1-3 | Propionic acid | 30 | 94 |
| | A1-4 | Lactic acid | 30 | 93 |
| | A1-5 | Inorganic salt medium (non-treated area) | — | 100 |

TABLE A2

| | | Plant-activating composition | | Test result | |
|---|---|---|---|---|---|
| | | Kind | Concentration (ppm) | Efficiency for absorbing a fertilizer | SPAD value |
| Inventive product | A2-1 | Myristic acid (LUNAC MY-98) | 100 | 130 | 114 |
| | | POE(20) sorbitan monooleate (RHEODOL TW-O120) | 500 | | |
| | A2-2 | Stearic acid (LUNAC S-98) | 50 | 142 | 118 |
| | | POE(20) sorbitan monooleate (RHEODOL TW-O120) | 150 | | |
| | A2-3 | Stearic acid (LUNAC S-98) | 50 | 147 | 122 |
| | | POE(20) sorbitan monooleate (RHEODOL TW-O120) | 150 | | |
| | | EDTA.4Na | 20 | | |
| | A2-4 | Oleic acid | 100 | 138 | 117 |
| | | POE(20) sorbitan monooleate (RHEODOL TW-O120) | 300 | | |
| | A2-5 | Behenic acid (LUNAC BA) | 100 | 122 | 110 |
| | | POE(20) sorbitan monooleate (RHEODOL TW-O120) | 150 | | |
| | A2-6 | Methyl laurate (EXCEPARL ML-85) | 50 | 126 | 109 |
| | | POE(20) sorbitan monooleate (RHEODOL TW-O120) | 150 | | |
| | A2-7 | 2-decyl-1-terta decanoic acid | 100 | 130 | 112 |
| | | POE(20) sorbitan monooleate (RHEODOL TW-O120) | 150 | | |
| | A2-8 | 2 Ethyl hexyl myristate | 400 | 132 | 111 |
| | | POE(20) sorbitan monooleate (RHEODOL TW-O120) | 600 | | |
| | A2-9 | Stearic stearate (EXCEPARL SS) | 100 | 139 | 112 |
| | | POE(20) sorbitan monooleate (RHEODOL TW-O120) | 200 | | |
| | A2-10 | Stearic stearate (EXCEPARL SS) | 100 | 144 | 115 |
| | | POE(20) sorbitan monooleate (RHEODOL TW-O120) | 200 | | |
| | | Malonic acid | 40 | | |
| | A2-11 | Ethylene glycol distearate (EMANON 3201M) | 150 | 140 | 114 |
| | | POE(20) sorbitan monooleate (RHEODOL TW-O120) | 400 | | |
| | A2-12 | POE(12) monolaurate (EMANON 1112) | 200 | 136 | 113 |
| | | POE(20) sorbitan monooleate (RHEODOL TW-O120) | 300 | | |
| | A2-13 | $C_{21}H_{43}COO(EO)_5COC_{17}H_{35}$ | 250 | 132 | 116 |
| | | POE(20) sorbitan monooleate (RHEODOL TW-O120) | 500 | | |
| | A2-14 | $C_{29}H_{59}COO(PO)_3(EO)_2COC_{17}H_{35}$ | 150 | 138 | 118 |
| | | POE(20) sorbitan monooleate (RHEODOL TW-O120) | 300 | | |
| | A2-15 | $C_{17}H_{33}COO(PO)_{15}H$ | 100 | 130 | 118 |
| | | POE(20) sorbitan monooleate (RHEODOL TW-O120) | 250 | | |
| Comparative product | A2-1 | Acetic acid | 50 | 90 | 96 |
| | | POE(20) sorbitan monooleate (RHEODOL TW-O120) | 150 | | |
| | A2-2 | Lactic acid | 100 | 92 | 94 |
| | | POE(20) sorbitan monooleate (RHEODOL TW-O120) | 300 | | |
| | A2-3 | Non-treated area (culturing solution only) | — | 100 | 100 |

TABLE A3

| | | Plant-activating composition | | Test result | |
|---|---|---|---|---|---|
| | | Kind | Concentration (ppm) | Fresh-weight | SPAD value |
| Inventive product | A3-1 | Stearic acid (LUNAC S-98) | 50 | 108 | 113 |
| | | POE(20) polyoxyethylene lauryl ether (EMULGEN 120) | 150 | | |
| | A3-2 | Stearic acid (LUNAC S-98) | 50 | 109 | 110 |
| | | POE(8) polyoxyethylene oleyl ether (EMULGEN 408) | 150 | | |
| | A3-3 | Stearic acid (LUNAC S-98) | 50 | 120 | 121 |
| | | POE(20) sorbitan monooleate (RHEODOL TW-O120) | 150 | | |
| | A3-4 | Stearic acid (LUNAC S-98) | 50 | 123 | 122 |
| | | POE(20) sorbitan monooleate (RHEODOL TW-O120) | 150 | | |
| | | EDTA.4Na | 20 | | |
| | A3-5 | Stearic stearate (EXCEPARL SS) | 50 | 119 | 120 |
| | | POE(6) sorbitan monolaurate (RHEODOL TW-L106) | 150 | | |
| | A3-6 | Stearic stearate (EXCEPARL SS) | 50 | 117 | 116 |
| | | POE(40) sorbit tetraoleate (RHEODOL 440) | 150 | | |
| | A3-7 | Stearic stearate (EXCEPARL SS) | 50 | 112 | 114 |
| | | Alkyl glycoside C10/C12/C14(MYDOL 12) | 150 | | |
| | A3-8 | Stearic stearate (EXCEPARL SS) | 50 | 116 | 117 |
| | | Alkyl glycoside (C10/C12/C14)(MYDOL 12) | 150 | | |
| | | Succinic acid | 20 | | |
| | A3-9 | Ethylene glycol distearate (EMANON 3201M) | 50 | 117 | 112 |
| | | Sodium POE(3) lauryl ether sulfate (EMAL 20C) | 150 | | |
| | A3-10 | Ethylene glycol distearate (EMANON 3201M) | 50 | 116 | 114 |
| | | Sodium POE(4.5) lauryl ether acetate (AKYPO RYM45NV) | 150 | | |

TABLE A3-continued

| | | Plant-activating composition | Concentration (ppm) | Test result | |
|---|---|---|---|---|---|
| | | Kind | | Fresh-weight | SPAD value |
| | A3-11 | Ethylene glycol distearate (EMANON 3201M) | 50 | 110 | 111 |
| | | Lauryl amide propyl betaine (AMPHITOL 20AB) | 150 | | |
| Comparative product | A3-1 | Acetic acid | 50 | 91 | 96 |
| | | POE(6) polyoxyethylene lauryl ether (EMULGEN 106) | 150 | | |
| | A3-2 | Propionic acid | 50 | 93 | 92 |
| | | POE (6) polyoxyethylene lauryl ether (EMULGEN 106) | 150 | | |
| | A3-3 | Caprylic acid | 50 | 94 | 95 |
| | | POE(6) polyoxyethylene lauryl ether (EMULGEN 106) | 150 | | |
| | A3-4 | Non-treated area (treated by only a liquid fertilizer) | — | 100 | 100 |

TABLE A4

| | | Plant-activating composition | Concentration (ppm) | Test result | |
|---|---|---|---|---|---|
| | | Kind | | Fresh-weight | SPAD value |
| Inventive product | A4-1 | Stearic acid (LUNAC S-98) | 100 | 107 | 111 |
| | | POE(20) polyoxyethylene lauryl ether (EMULGEN 120) | 200 | | |
| | A4-2 | Cerotic acid | 100 | 109 | 110 |
| | | POE(8) polyoxyethylene oleyl ether (EMULGEN 408) | 200 | | |
| | A4-3 | Stearic acid (LUNAC S-98) | 100 | 129 | 120 |
| | | POE(20) sorbitan monooleate (RHEODOL TW-O120) | 200 | | |
| | A4-4 | Stearic acid (LUNAC S-98) | 100 | 132 | 126 |
| | | POE(20) sorbitan monooleate (RHEODOL TW-O120) | 200 | | |
| | | EDTA.4Na | 30 | | |
| | A4-5 | Stearic stearate (EXCEPARL SS) | 100 | 118 | 121 |
| | | POE(6) sorbitan monolaurate (RHEODOL TW-L106) | 200 | | |
| | A4-6 | Stearic stearate (EXCEPARL SS) | 100 | 117 | 118 |
| | | POE(40) sorbit tetraoleate (RHEODOL 440) | 200 | | |
| | A4-7 | Stearic stearate (EXCEPARL SS) | 100 | 114 | 116 |
| | | Alkyl glycoside (C10/C12/C14)(MYDOL 12) | 200 | | |
| | A4-8 | Stearic stearate (EXCEPARL SS) | 100 | 116 | 118 |
| | | Alkyl glycoside (C10/C12/C14)(MYDOL 12) | 200 | | |
| | | Malic acid | 30 | | |
| | A4-9 | Methyl laurate (EXCEPARL ML-85) | 100 | 122 | 114 |
| | | Sodium POE(3) lauryl ether sulfate (EMAL 20C) | 200 | | |
| Comparative product | A4-1 | Acetic acid | 100 | 92 | 94 |
| | | POE(6) polyoxyethylene lauryl ether (EMULGEN 106) | 200 | | |
| | A4-2 | Propionic acid | 100 | 95 | 93 |
| | | POE(6) polyoxyethylene lauryl ether (EMULGEN 106) | 200 | | |
| | A4-3 | Non-treated area (treated by only water) | — | 100 | 100 |

In the Tables, POE is an abbreviation of polyoxyethylene. The number in the parentheses is the average number of ethylene oxide moles added. The wording in the parentheses subsequent to the kinds of the activating agents and the compositions represents a tradename of a product supplied by Kao Corp.

Example B1

<Test of Reproductive Ability Using Chlorella Cells>

Example B2

<Test of Hydroponics of Tomato Seedlings>

Example B3

<Test of Soil-Treatment for Tomatoes>

Example B4

<Test of Soil-Treatment for Spinach>

Examples B1 to B4 were carried out by the same manner as in Examples 1 to 4 except that the plant-activating agents described in Tables B1 to B4 were used. Results are shown in Tables B1 to B4 respectively.

TABLE B1

| | | Plant-activating agent or plant-activating composition | | Evaluation result |
|---|---|---|---|---|
| | | Kind | Concentration (ppm) | reproductive ability |
| Inventive product | B1-1 | Tallow | 30 | 124 |
| | B1-2 | Batyl alcohol | 30 | 138 |
| | | EDTA·4Na | 4 | |
| | B1-3 | Stearic acid monoglyceride | 30 | 132 |
| | B1-4 | Batyl alcohol | 30 | 130 |
| | B1-5 | Palm oil | 30 | 124 |
| | B1-6 | Glyceric acid stearyl ester | 30 | 122 |
| | B1-7 | Glyceric acid cetyl amide | 30 | 120 |
| | B1-8 | Hexaglycerol ester of stearic acid | 30 | 123 |
| | B1-9 | Glycerol carbonate | 30 | 126 |
| Comparative product | B1-1 | Glycerol | 30 | 98 |
| | B1-2 | Inorganic salt medium (non-treated area) | — | 100 |

TABLE B2

| | | Plant-activating composition | | Test result | |
|---|---|---|---|---|---|
| | | Kind | Concentration (ppm) | Effiency for absorbing a fertilizer | SPAD value |
| Inventive product | B2-1 | Stearic acid diglyceride | 100 | 134 | 114 |
| | | POE(20) sorbitan monooleate | 500 | | |
| | B2-2 | Palmitic acid/stearic acid monoglyceride (EXCEL VS-95) | 50 | 130 | 112 |
| | | POE(20) sorbitan monooleate | 150 | | |
| | B2-3 | Oleic acid monoglyceride | 50 | 128 | 114 |
| | | POE(20) sorbitan monooleate | 150 | | |
| | B2-4 | Stearic acid diglyceride | 100 | 139 | 117 |
| | | POE(20) sorbitan monooleate | 300 | | |
| | | EDTA.4Na | 20 | | |
| | B2-5 | Tallow | 100 | 122 | 110 |
| | | POE(20) sorbitan monooleate | 150 | | |
| | B2-6 | Palm oil | 50 | 125 | 109 |
| | | POE(20) sorbitan monooleate | 150 | | |
| | B2-7 | Oleic acid mono/diglyceride (EXCEL 300) | 100 | 126 | 112 |
| | | POE(20) sorbitan monooleate | 150 | | |
| | B2-8 | Batyl alcohol | 50 | 132 | 115 |
| | | POE(20) sorbitan monooleate | 600 | | |
| | B2-9 | Glyceric acid stearyl ester | 100 | 121 | 113 |
| | | POE(20) sorbitan monooleate | 200 | | |
| | B2-10 | Glyceric acid stearyl ester | 100 | 128 | 116 |
| | | POE(20) sorbitan monooleate | 200 | | |
| | | Malonic acid | 40 | | |
| | B2-11 | Stearic acid monoglyceride | 300 | 130 | 112 |
| | | POE(20) sorbitan monooleate | 300 | | |
| | B2-12 | Glyceric acid stearyl amide | 150 | 124 | 111 |
| | | POE(20) sorbitan monooleate | 400 | | |
| Comparative product | B2-1 | Glycerol | 100 | 98 | 99 |
| | | POE(20) sorbitan monooleate | 300 | | |
| | B2-2 | Culturing solution only (non-treated area) | — | 100 | 100 |

TABLE B3

| | | Plant-activating composition | | Test result | |
|---|---|---|---|---|---|
| | | Kind | Concentration (ppm) | Fresh-weight | SPAD value |
| Inventive product | B3-1 | Batyl alcohol | 50 | 123 | 118 |
| | | POE(20) lauryl ether | 150 | | |
| | B3-2 | Glyceric acid stearyl ester | 50 | 119 | 118 |
| | | POE(8) oleyl ether | 150 | | |
| | B3-3 | Glyceric acid stearyl amide | 50 | 115 | 116 |
| | | POE(20) sorbitan monooleate | 150 | | |
| | B3-4 | Batyl alcohol | 50 | 126 | 120 |
| | | POE(20) sorbitan monooleate | 150 | | |
| | | EDTA.4Na | 20 | | |

TABLE B3-continued

| | | Plant-activating composition | | Test result | |
|---|---|---|---|---|---|
| | | Kind | Concentration (ppm) | Fresh-weight | SPAD value |
| | B3-5 | Stearic acid monoglyceride | 50 | 122 | 117 |
| | | POE(6) sorbitan monolaurate | 150 | | |
| | B3-6 | Palm-stearin oil acid | 50 | 118 | 115 |
| | | POE(40) sorbit tetraoleate | 150 | | |
| | B3-7 | Oleic acid mono/diglyceride (EXCEL 300) | 50 | 112 | 113 |
| | | Alkyl glycoside (MYDOL 12 supplied by Kao Corp.) | 150 | | |
| | B3-8 | Stearic acid monoglyceride | 50 | 124 | 119 |
| | | Alkyl glycoside (MYDOL 12) | 150 | | |
| | | Succinic acid | 20 | | |
| | B3-9 | Tallow | 50 | 118 | 116 |
| | | Sodium POE(3) lauryl ether sulfate | 150 | | |
| | B3-10 | Hexaglycerol ester of stearic acid | 50 | 119 | 114 |
| | | POE(40) sorbit tetraoleate (RHEODOL 440) | 150 | | |
| | B3-11 | Glycerol carbonate | 50 | 119 | 113 |
| | | Sodium POE(4.5) lauryl ether acetate | 150 | | |
| | B3-12 | Palmitic acid/stearic acid monoglyceride (EXCEL VS-95) | 50 | 114 | 111 |
| | | Lauryl amide propyl betaine | 150 | | |
| Comparative product | B3-1 | Glycerol | 50 | 95 | 100 |
| | | POE(8) oleyl ether | 150 | | |
| | B3-2 | Glycerol | 50 | 98 | 99 |
| | | Alkyl glycoside (MYDOL 12) | 150 | | |
| | B3-3 | Treated with a liquid fertilizer (non-treated area) | — | 100 | 100 |

TABLE B4

| | | Plant-activating composition | | Test result | |
|---|---|---|---|---|---|
| | | Kind | Concentration (ppm) | Fresh-weight | SPAD value |
| Inventive product | B4-1 | Oleic acid monoglyceride | 100 | 120 | 115 |
| | | POE(20) lauryl ether | 200 | | |
| | B4-2 | Stearic acid monoglyceride | 100 | 130 | 122 |
| | | POE(8) oleyl ether | 200 | | |
| | B4-3 | Tallow | 100 | 128 | 120 |
| | | POE(20) sorbitan monooleate | 200 | | |
| | B4-4 | Stearic acid monoglyceride | 100 | 135 | 125 |
| | | POE(20) sorbitan monooleate | 200 | | |
| | | EDTA · 4Na | 30 | | |
| | B4-5 | Palm-stearin oil | 100 | 122 | 120 |
| | | POE(6) sorbitan monolaurate | 200 | | |
| | B4-6 | Oleic acid mono/diglyceride (EXCEL 300) | 100 | 120 | 119 |
| | | POE(40) sorbit tetraoleate | 200 | | |
| | B4-7 | Batyl alcohol | 100 | 124 | 115 |
| | | Alkyl glycoside (MYDOL 12) | 200 | | |
| | B4-8 | Glyceric acid stearyl ester | 100 | 130 | 119 |
| | | Alkyl glycoside (MYDOL 12) | 200 | | |
| | | Malic acid | 30 | | |
| | B4-9 | Glyceric acid stearyl amide | 100 | 121 | 113 |
| | | Sodium POE(3) lauryl ether sulfate | 200 | | |
| | B4-10 | Glycerol carbonate | 100 | 129 | 120 |
| | | POE(6) sorbitan monolaurate | 200 | | |
| | B4-11 | Hexaglycerol ester of stearic acid | 100 | 125 | 118 |
| | | POE(8) oleyl ether | 200 | | |
| Comparative product | B4-1 | Glycerol | 100 | 98 | 99 |
| | | Sodium POE(3) lauryl ether sulfate | 200 | | |
| | B4-2 | Treated by water (non-treated area) | — | 100 | 100 |

In the Tables, POE is an abbreviation of polyoxyethylene and the number in the parentheses is the average number of ethylene oxide moles added. The wording in the parentheses subsequent to the activating agents and the compositions represents a tradename of a product supplied by Kao Corp.

Example C1

<Test of Soil-Treatment for Tomato Seedlings>

Seeds of tomato "Momotaro" were sown in a cell tray using Kureha Engei Baido [horticultural soil supplied by Kureha Chemical Industry Co., Ltd.; the fertilizer components: N:P:K=0.4:1.9:0.6 (g/kg)] as the cultural soil. After true leaves expanded, the seedlings were fixedly planted in pots having a diameter of 12 cm. Then, the treatment was started. That is, the plant-activating compositions, in which starting ingredients shown in Table C1 and OKF2 (supplied by Otsuka Chemical Co., Ltd.) as a fertilizer component in concentration of 230 ppm (2000-fold diluted solution) were blended, were used to treat the soil with the treating amount of 60 ml/individual every 7 days 4 times in total. The blended concentrations of the starting ingredients were as shown in Table C1 and the balance was water. After 6 days from the 4 treatments, the fresh-weight and the SPAD value (SPAD502 supplied by Minolta Co., Ltd.) showing the green degree of leaves of the plants were measured. The measured values as the relative values were compared, when that of the non-treated was made as 100. The fertilizer composition of OKF2 (supplied by Otsuka Chemical Co., Ltd.) was that N:P:K:Ca:Mg=14:8:16:6:2. In the present example, however, the number of the individuals was 10, the result of the fresh-weight was the average of 10 data thereof, and the result of the SPAD value was the average of 30 data (that is, 3 points were measured every individuals) measured about the third true leaf.

be random or block; n represents an average number of moles added and is 1 to 30; and wherein the plant-activating agent is in an aqueous solution or aqueous dispersion and is in a concentration of 50 to 500 ppm.

2. The method of activating a plant as claimed in claim 1, wherein said composition comprises 10 to 5,000 parts by weight of the fertilizer component per 100 parts by weight of the activating agent.

3. The method of activating a plant as claimed in claim 2, wherein said composition further comprises 10 to 5,000 parts by weight of other nutrients per 100 parts by weight of the activating agent.

4. The method of activating a plant as claimed in claim 1, wherein R represents an alkyl or alkenyl group having 15 to 21 carbon atoms.

5. The method of activating a plant as claimed in claim 1, wherein the plant activating composition further comprises a surfactant which is at least one selected from the group consisting of: sorbitan fatty acid esters, polyoxyalkylene sorbitan

TABLE C1

|  | No. | Plant-activating composition | Concentration (ppm) | Test result Fresh-weight | SPAD value |
|---|---|---|---|---|---|
| Inventive product | C-1 | Batyl alcohol<br>POE(60) polyoxyethylene hardened (or hydrogenated) cast oil [EMANON CH-60(K)] | 50<br>150 | 112 | 107 |
|  | C-2 | Batyl alcohol<br>POE(80) polyoxyethylene hardened caster oil [EMANON CH-80] | 50<br>150 | 125 | 114 |
|  | C-3 | Batyl alcohol<br>POE(80) polyoxyethylene hardened caster oil [EMANON CH-80]<br>Citric acid | 50<br>150<br>20 | 128 | 116 |
|  | C-4 | Stearic acid<br>POE(20) sorbitan monooleate [RHEODOL TW-O120] | 50<br>150 | 120 | 109 |
|  | C-5 | Stearic acid<br>POE(20) sorbitan monooleate [RHEODOL TW-O120]<br>Citric acid 3Na salt | 50<br>150<br>20 | 124 | 112 |
|  | C-6 | Citric acid C18 monoamide<br>Sucrose fatty acid ester [DK ester F160$^{\times}$] | 50<br>150 | 123 | 111 |
|  | C-7 | Citric acid C18 monoamide<br>Sucrose fatty acid ester [DK ester F140$^{\times}$] | 50<br>150 | 121 | 110 |
|  | C-8 | Glyceric acid stearyl ester<br>POE(20) sorbitan tristearate [RHEODOL TW-S320] | 50<br>150 | 120 | 112 |
|  | C-9 | Glyceric acid stearyl ester<br>POE(12) stearyl ether [EMULGEN 320P] | 50<br>150 | 111 | 106 |
|  | C-10 | Citric acid C18 monoamide<br>Sucrose fatty acid ester [DK ester F160$^{\times}$]<br>Potassium oxalate | 50<br>150<br>20 | 126 | 114 |
| Comparative product | C-1 | Glycerol<br>POE(5) lauryl ether [EMULGEN 106] | 50<br>150 | 96 | 97 |
|  | C-2 | Lactic acid<br>POE(5) lauryl ether [EMULGEN 106] | 50<br>150 | 93 | 94 |
|  | C-3 | Acetic acid<br>POE(5) lauryl ether [EMULGEN 106] | 50<br>150 | 91 | 92 |
|  | Treated with a liquid fertilizer (non-treated) |  | — | 100 | 100 |

In the Tables, POE is an abbreviation of polyoxyethylene and the number in the parentheses is the average number of ethylene oxide moles added. The wording in the brackets represents a tradename of a product supplied by Kao Corp. In particular, the mark $^{\times}$ is a tradename of Dai-Ichi Kogyo Seiyaku Co., Ltd.

The invention claimed is:

1. A method of activating a plant by applying to a plant a plant-activating composition comprising a plant-activating agent and a fertilizer component, said plant-activating agent is a compound of formula (II), $$RCOO(AO)_nX^1 \qquad (II)$$

wherein R represents an alkyl or alkenyl group having 13 to 21 carbon atoms; $X^1$ represents an alkyl or acyl group having 1 to 22 carbon atoms or an alkenyl group having 2 to 22 carbon atoms; AO represents at least one group selected from oxyethylene, oxypropylene and oxybutylene groups and may fatty acid esters, polyoxyalkylene fatty acid esters, polyoxyalkylene glycerol fatty acid esters, polyglycerol fatty acid esters, polyoxyalkylene polyglycerol fatty acid esters, sucrose fatty acid esters, resin acid esters, polyoxyalkylene resin acid esters, polyoxyalkylene alkyl ethers, polyoxyalkylene alkylphenyl ethers, polyoxyalkylenealkyl(poly)glycosides, polyhydric carboxylic acid salts, polyoxyalkylene alkyl ether carboxylic acid salts, polyoxyalkylene alkylamide ether carboxylic acid salts, rhodinic acid salts, alkylbenezenesulfonates, alkyl sulfonates, alkylnaphthalenesulfonates, naphthalenesulfonates, diphenyl ether sulfonic acid salts, condensates of alkylnaphthalenesulfonates, condensates of naphthalenesulfonates, alkylsulfates, polyoxyalkylene alkylsulfates, polyoxyalkylene alkyl phenyl ether sulfuric acid salts, tristyrenated phenol sulfuric acid ester salts, polyoxyalkylene distyrenated phenol sulfuric acid ester salts, alkylpolyglycoside sulfuric acid salts, alkylphenylphosphoric acid ester salts, polyoxyalkylene alkylphosphoric acid ester salts, polyoxyalkylene alkylpheneylphosphoric acid ester salts, amino acid group-containing surfactants, betaine group-containing surfactants, imidazoline group-containing surfactants, amine oxide group-containing surfactants and acylamino acid salts.

6. The method of activating a plant as claimed in claim 1, wherein the fertilizer is inorganic or organic compound which can supply at least one elements selected from N, P, K, Mg, S, B, Fe, Mn, Cu, Zn, Mo, Cl, Si and Na.

7. The method of activating a plant as claimed in claim 1, wherein n is 1 to 20.

8. The method of activating a plant as claimed in claim 1, wherein n is 1 to 10.

9. The method of activating a plant as claimed in claim 1, wherein n is 1.

* * * * *